United States Patent
Chiba

(10) Patent No.: US 8,775,096 B2
(45) Date of Patent: Jul. 8, 2014

(54) AUXILIARY DIAGNOSTIC APPARATUS AND AUXILIARY DIAGNOSTIC METHOD

(75) Inventor: Toru Chiba, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/499,395

(22) PCT Filed: Oct. 22, 2010

(86) PCT No.: PCT/JP2010/068663
§ 371 (c)(1),
(2), (4) Date: Mar. 30, 2012

(87) PCT Pub. No.: WO2011/052491
PCT Pub. Date: May 5, 2011

(65) Prior Publication Data
US 2012/0191365 A1     Jul. 26, 2012

(30) Foreign Application Priority Data

Oct. 29, 2009 (JP) ................................. 2009-248660

(51) Int. Cl.
| | | |
|---|---|---|
| G01N 33/48 | (2006.01) | |
| G01N 33/50 | (2006.01) | |
| G06F 19/00 | (2011.01) | |
| G06F 19/12 | (2011.01) | |
| G06F 17/10 | (2006.01) | |
| G06F 17/11 | (2006.01) | |

(52) U.S. Cl.
CPC ............ *G06F 19/3437* (2013.01); *G06F 19/12* (2013.01); *G06F 17/10* (2013.01); *G06F 17/11* (2013.01)
USPC .............................................. 702/19; 702/22

(58) Field of Classification Search
None
See application file for complete search history.

(56) References Cited

U.S. PATENT DOCUMENTS

| | | |
|---|---|---|
| 6,280,381 B1 | 8/2001 | Malin et al. |
| 2004/0073119 A1 | 4/2004 | Mycek et al. |
| 2009/0252406 A1* | 10/2009 | Chiba ........................... 382/165 |

FOREIGN PATENT DOCUMENTS

| | | |
|---|---|---|
| CN | 1882278 | 12/2006 |
| JP | 2002-535023 A | 10/2002 |
| JP | 2005-504561 A | 2/2005 |
| JP | 2007-135989 A | 6/2007 |
| JP | 2009-082736 A | 4/2009 |
| WO | 00/42907 | 7/2000 |
| WO | 02/069784 A2 | 9/2002 |
| WO | 2005/045393 A2 | 5/2005 |
| WO | 2005/045393 A3 | 5/2005 |

OTHER PUBLICATIONS

Skoog et al. Fundamentals of Analytical Chemistry, Sixth Edition. New York: Saunders College Publishing, 1992, pp. 8-9.*

(Continued)

*Primary Examiner* — Russell S Negin
(74) *Attorney, Agent, or Firm* — Greenblum & Bernstein, P.L.C.

(57) ABSTRACT

Disclosed is an auxiliary diagnostic apparatus including: a vector input unit that reads a test vector which is a spectral property vector of a biological tissue targeted for a diagnosis; a multiple linear regression analysis unit that executes a multiple liner regression analysis for the test vector with a plurality of individual component vectors which are spectral property vectors of particular substances, and obtains an error vector which is a vector of a residual error component; and an indicator calculation unit that extracts a feature of the error vector, and, from the extracted error vector, calculates an indicator representing whether an affected area is included in the biological tissue targeted for the diagnosis and which type of affected area has a possibility of being included in the biological tissue.

10 Claims, 3 Drawing Sheets

(56) References Cited

OTHER PUBLICATIONS

Golub et al. Molecular classification of cancer: Class discovery and class prediction by gene expression monitoring. Science, vol. 286, 1999, pp. 531-537.*

English Abstract of JP 2002-535023.

English Abstract of JP 2005-504561.

Etsuhiro Matsuyama et al., "The Standard value of lumbar bone mineral density and diagnosis of osteoporosis" Central Japan Journal of Orthopaedic Surgery & Traumatology, Jan. 1, 1994, vol. 37, No. 1, pp. 199 to 200 (With English Translation).

China Office action, dated Jan. 28, 2014 along with an english translation thereof.

* cited by examiner

AUXILIARY DIAGNOSTIC APPARATUS AND AUXILIARY DIAGNOSTIC METHOD

TECHNICAL FIELD

The present invention relates an auxiliary diagnostic apparatus and an auxiliary diagnostic method for obtaining, from a spectral property of a biological tissue such as a mucous membrane, an indicator concerning whether the biological tissue includes an affected area and which type of affected area the biological tissue includes.

BACKGROUND ART

In recent years, an electronic endoscope having the function as a spectrometer described, for example, in Japanese Patent Provisional Publication No. JP2007-135989A has been proposed. Through the electronic endoscope of this type, a spectral property (distribution of an optical absorption factor with respect to frequency) of a biological tissue, such as a mucous membrane of a digestive organ, e.g., a stomach or an intestinum rectum can be obtained. The spectral property depends on types of substances included in a surface layer of the biological tissue target for measurement of the spectral property (Beer-Lambert Law). That is, the spectral property of a biological tissue is obtained by combining the spectral properties of a plurality of primary substances forming the biological tissue.

There is a case where, substances which are rare in a biological tissue of a healthy portion are included in a great amount in a biological tissue of an affected area. Therefore, the spectral property of a biological tissue including an affected area differs from the spectral property of a biological tissue including only a health portion. As a result, by comparing the spectral property of a biological tissue with the spectral property of a known tissue not including an affected area, it becomes possible to make a diagnosis as to whether the biological tissue includes an affected area.

SUMMARY OF THE INVENTION

Conventionally, a diagnosis was conducted by a doctor by visually checking a graph of the spectral property of a biological tissue measured by a spectrometer. The above described diagnosis through visual checking depends exclusively on the doctor's experience. Therefore, it has been desired to provide an auxiliary diagnostic apparatus and an auxiliary diagnostic method capable of obtaining an indicator serving as a quantitative judgment material in a diagnosis using a spectral property.

The object of the present invention is to provide an auxiliary diagnostic apparatus and an auxiliary diagnostic method capable of solving the above described problem, i.e., capable of obtaining a quantitative indicator in a diagnosis using a spectral property.

To achieve the above described object, an auxiliary diagnostic apparatus according to the invention comprises: a vector input means that reads a test vector which is a spectral property vector of a biological tissue targeted for a diagnosis; a multiple linear regression analysis means that executes a multiple liner regression analysis for the test vector with a plurality of individual component vectors which are spectral property vectors of particular substances, and obtains an error vector which is a vector of a residual error component; and an indicator calculation means that extracts a feature of the error vector, and, from the extracted error vector, calculates an indicator representing whether an affected area is included in the biological tissue targeted for the diagnosis and which type of affected area has a possibility of being included in the biological tissue.

With this configuration, it becomes possible to obtain the indicator which is used as a quantitative judgment material in the diagnosis and which is calculated based on the error vector of the spectral property component not included in a healthy tissue.

Preferably, the individual component vectors are calculated by an individual component analysis from spectral property vectors of a plurality of biological tissue samples each of which corresponds to a same portion of the biological tissue targeted for the diagnosis and which does not include an affected area.

Preferably, the indicator calculation means calculates the indicator based on an affected area substance vector obtained by the individual component analysis from affected area sample error vectors which are vectors of residual error components obtained by executing, with the plurality of individual component vectors, the multiple linear regression analysis for spectral property vectors of a plurality of biological tissue samples including particular affected areas.

The indicator calculation means may operate to:
calculate, by the multiple liner regression analysis, a coefficient $s_d$ satisfying a following expression (a):

$$E \approx s_d E_d \quad (a)$$

where the error vector is defined as $E=[E_{\lambda 1}, E_{\lambda 2}, \ldots E_{\lambda M}]$ and the affected area substance vector is defined as $Ed=[E_{d\lambda 1}, E_{d\lambda 2}, \ldots E_{d\lambda M}]$; calculate, using a weighing coefficient $w_{\lambda m}$, a similarity D between vectors $E/s_d$ and $E_d$ through a following expression (b):

$$D = \sum_{m=1}^{M} w_{\lambda m} \cdot \left(E_{d\lambda m} - \frac{E_{\lambda m}}{s_d}\right)^2 ; \quad (b)$$

and
determine the indicator based on the similarity D.

The indicator calculation means may operate to:
calculate a probability that the similarity D is included in a similarity group $D_{dk}$, by a test based on a coefficient $S_{dk}$, satisfying a following expression (c) and obtained by the multiple liner regression analysis while defining the plurality of affected area sample error vectors as $E_{dk}=[E_{dk\lambda 1}, E_{dk\lambda 2}, \ldots E_{dk\lambda M}]$ (k=1, 2, ..., K), and the similarity group $D_{dk}$ between $E_d$ and respective ones of vectors $E_{dk}/s_{dk}$ obtained by a following expression (d); and
define the probability that the similarity D is included in the similarity group $D_{dk}$ as the indicator.

$$E_{dk} \approx s_{dk} E_d \quad (c)$$

$$D_{dk} = \sum_{m=1}^{M} w_{\lambda m} \cdot \left(E_{d\lambda m} - \frac{E_{dk\lambda k}}{s_{dk}}\right)^2 \quad (d)$$

As described above according to the invention, an auxiliary diagnostic apparatus and an auxiliary diagnostic method capable of obtaining a quantitative indicator in a diagnosis using a spectral property.

EMBODIMENTS FOR CARRYING OUT THE INVENTION

Figure 1:
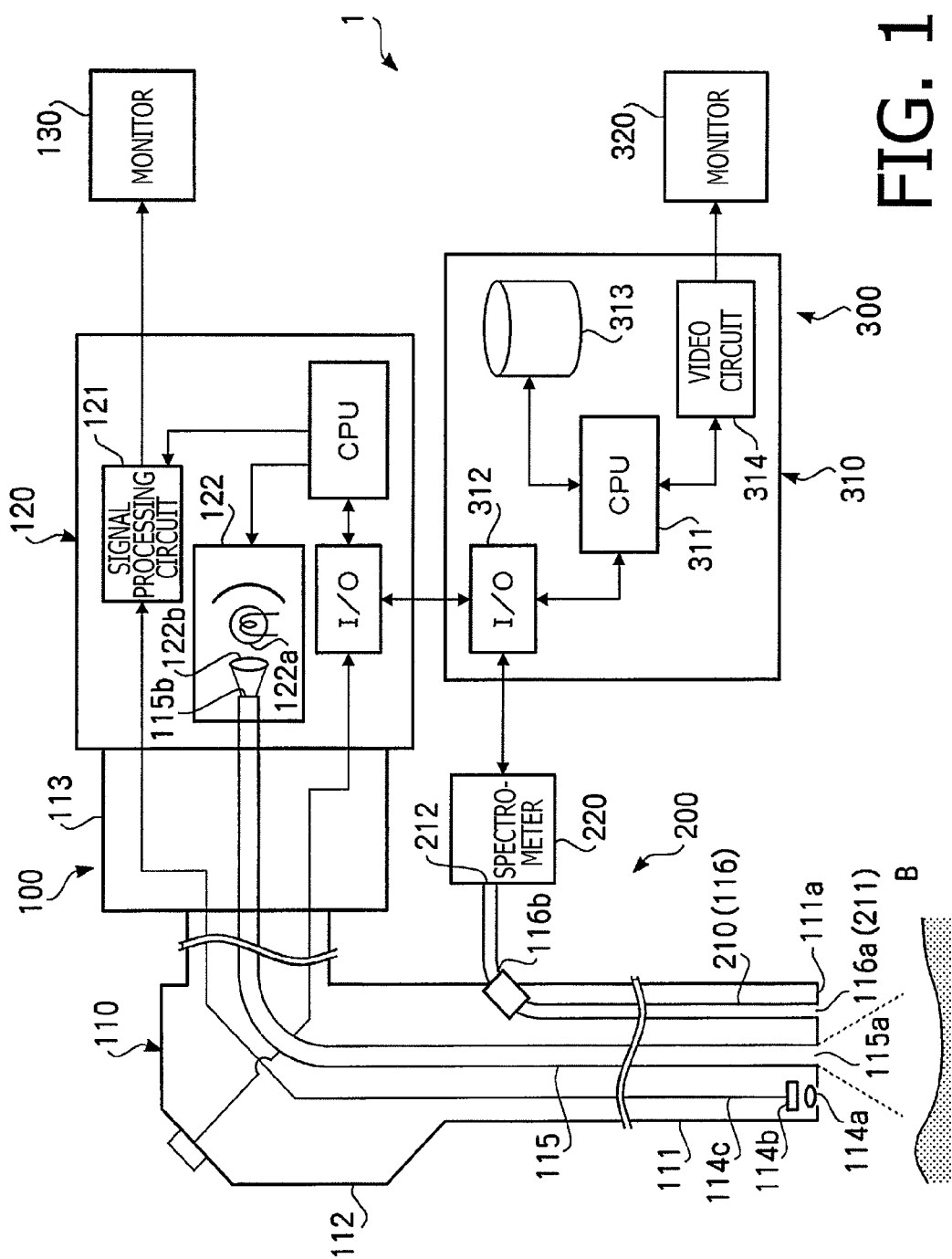
FIG. 1 is a block diagram of an auxiliary diagnostic system according to an embodiment of the invention.

In the following, an embodiment according to the present invention is explained with reference to the accompanying drawings. FIG. 1 is a block diagram of an auxiliary diagnostic system according to the embodiment. An auxiliary diagnostic system 1 according to the embodiment includes an electronic endoscope 110, an electronic endoscope device 100 having an electronic endoscope processor 120 and an endoscope image monitor 130, a spectrometer device 200 including a spectro-probe 210 and a spectrometer 220, and an analyzing device 300 including an analysis computer 310 and an analysis result displaying monitor 320.

The electronic endoscope 110 includes an insertion tube 111, an operation unit 112 and a connector 113. In a tip part 111a of the insertion tube 111, an objective optical system 114 and a solid state image pick-up device 114 are accommodated. An image of a body cavity surface B around the tip part 111a of the insertion tube is converged by the objective optical system 114a onto a photo-acceptance part of the solid state image pick-up device 114b. Through photoelectric transfer, the solid state image pick-up device 114a generates a video signal corresponding to the image formed on the photo-acceptance surface. The generated video signal is transmitted to the electronic endoscope processor 120 via a solid state image pick-up device cable 114c arranged throughout the insides of the insertion tube 111, the operation unit 112 and the connector 113. As a solid state image pick-up device, a device using a CCD or a CMOS can be employed.

The solid state image pick-up device cable 114c is connected to a signal processing circuit 121 accommodated in the electronic endoscope processor 120. The signal processing circuit 121 generates a video signal (e.g., an NTSC signal) in a predetermined format by processing the video signal generated by the solid state image pick-up device 114b, and transmits the generated video signal to the endoscope image monitor 130 connected to the electronic endoscope processor 120. As a result, the image of the body cavity surface B around the tip part 111a of the insertion tube picked up by the solid state image pick-up device 114b is displayed on the endoscope image monitor 130.

A light guide 115 such as an optical fiber bundle is provided throughout the insides of the insertion tube 111, the operation unit 112 and the connector 113. A tip 115a of the light guide 115 faces a cover glass (not shown) provided at the tip part 111a of the insertion tube. A proximal end 115b of the light guide 115 protrudes from the connector 113, and when the connector 113 is attached to the electronic endoscope processor 120, the proximal end 115b is inserted into the inside of the electronic endoscope processor 120.

In the electronic endoscope processor 120, a light source unit 122 having a lamp 122a and a condenser lens 122b is accommodated. In a state where the connector 113 of the electronic endoscope 110 is connected to the electronic endoscope processor 120, illumination light produced by the lamp 122a is incident on the proximal end 115b of the light guide 115 by the condenser lens 122b. The illumination light which has entered the proximal end 115b proceeds through the light guide 115, is emitted from the tip 115a through the cover glass, and illuminates the body cavity surface B around the tip part 111a of the insertion tube.

In the insertion tube 111 of the electronic endoscope 110, a forceps channel 116 is accommodated. A tip 116a of the forceps channel 116 is opened at the tip part 111a of the insertion tube, and a proximal end of the forceps channel 116 is formed as a forceps hole 116b provided at the midway point of the insertion tube 111.

In this embodiment, the spectro-probe 210 is inserted into the forceps channel 116 from the forceps hole 116b. A tip 211 of the spectro-probe 210 is arranged at the tip 116a of the forceps channel 116. A proximal end 212 of the spectro-probe 210 is connected to the spectrometer 220. The spectro-probe 210 is a sort of a light guide having a condenser lens at a tip thereof, and part of reflected light reflected from the body cavity surface B (or the inside of the body cavity) enters the spectro-probe 210 via the condenser lens, and is transmitted to the spectrometer 220.

The spectrometer 220 measures the spectral property of light transmitted from the spectro-probe 210. Data of the measured spectral property is transmitted to the analysis computer 310.

The analysis computer 310 includes a CPU 311, an I/O controller 312, a storage 313 and a video circuit 314. The analysis computer 310 is, for example, a personal computer or a workstation.

The CPU 311 of the analysis computer 310 obtains data of the spectral property by the spectrometer 220 via the I/O controller 312. By executing an analysis program which is descried later, the analysis computer 310 obtains an analysis result indicating whether the body cavity surface B has an affected area or which type of affected area has a high possibility of occurrence. Further, the CPU 311 controls the video circuit 314, and displays the analysis result data on the analysis result displaying monitor 320.

Hereafter, the analysis program executed by the CPU 311 of the analysis computer is explained.

Figure 2:
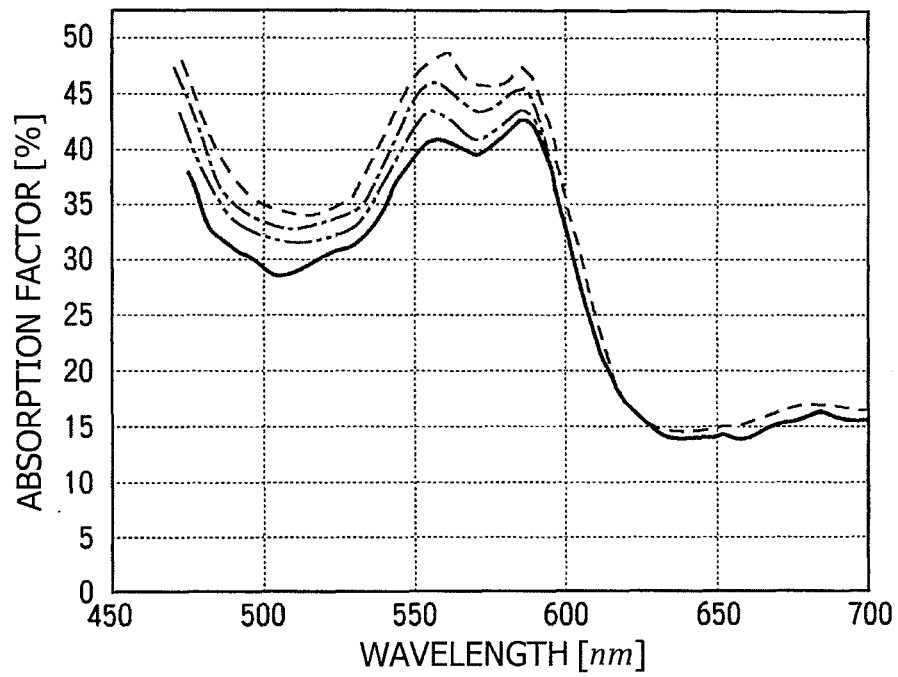
FIG. 2 is a graph illustrating an example of a spectral property of a mucous membrane of a healthy stomach.

FIG. 2 is a graph illustrating an example of the spectral property (i.e., the optical absorption factor with respect to the frequency) of a mucous membrane of a healthy stomach. As shown in FIG. 2, the mucous membrane of the healthy stomach has peaks in the parts smaller than or equal to 480 nm, 550 nm to 560 nm and 580 nm to 590 nm, although a small degree of fluctuation is caused depending on the individual differences or the observation position. It is said that the spectral property of a biological tissue is determined by substances forming a surface layer of a portion targeted for observation of the spectral property. For example, the spectral property of hemoglobin bound to oxygen has the peaks at around 540 nm and the range of 570 nm to 580 nm, and the spectral property (i.e., the spectral property of a vein) of hemoglobin not bound to oxygen has a peak in the range of 550 nm to 560 nm.

A biological tissue is formed of various types of substances including components of body fluid, such as erythrocytes and substances forming a cell. In a healthy tissue, there is almost no difference, caused by individual differences or the observation position, in the type of principal substances forming a particular biological tissue, and the difference in spectral property by the individual differences depends on the ratio between substances forming the tissue. That is, when N represents the number of types of principal substances forming a biological tissue, and $\epsilon_n$ (n=1, 2, ..., N) represents a spectral property vector of each substance (individual component) (a vector of the optical absorption factor measured at every particular frequency (e.g., 5 nm) in a particular frequency band (e.g., 470 nm to 700 nm)), a spectral property vector $x_h$ of a particular healthy biological tissue is approximated by the following expression 1.

$$x_h \approx \sum_{n=1}^{N} s_n \varepsilon_n \quad \text{(Expression 1)}$$

In the above described expression 1, the coefficients $s_n$ vary between samples depending on, for example, the individual differences.

On the other hand, a biological tissue of an affected area includes substances not included in a healthy biological tissue, and the types of the affected areas differ depending on conditions of the types of the affected areas. That is, a spectral property vector $x_u$ of an affected area is approximated by a following expression 2.

$$x_u \approx \sum_{n=1}^{N} s_n \varepsilon_n + E \quad \text{(Expression 2)}$$

Therefore, if it is possible to determine the coefficient $s_r$, satisfying the expression 1 with respect to a spectral property vector A of a particular biological tissue, it can be said that the biological tissue has a high possibility of a healthy tissue. On the other hand, if it is not possible to determine the coefficient $s_n$ with respect to the spectral property vector A, and an error component E which is a residual error remains, the biological tissue has a high possibility of an affected area. The feature (e.g., the peak frequency) of the error component E is determined depending on the type of the affected area. Therefore, it becomes possible to estimate the type of the affected area from the feature of the error component E.

Figure 3:
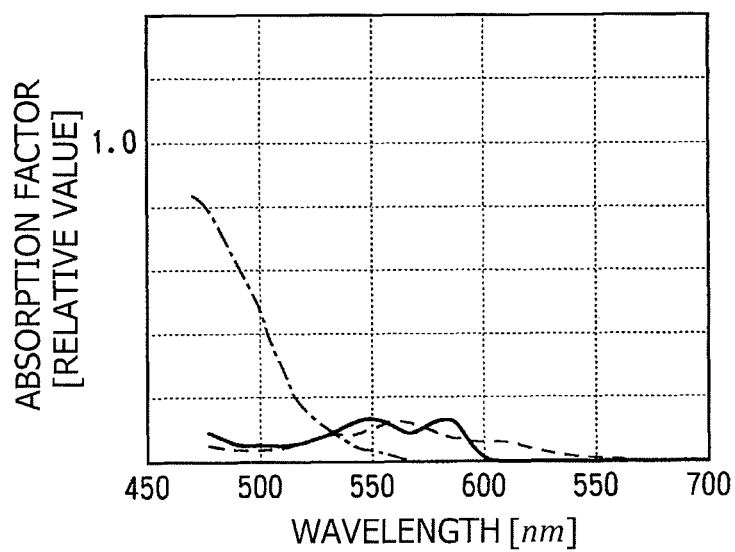
FIG. 3 is a graph of an analysis result of an individual component of the spectral property of the mucous membrane of the stomach shown in FIG. 2.

Since the individual component vector $\varepsilon_n$ can be regarded as having no relationship with respect to each other, the individual component vector $\varepsilon_n$ can be estimated by measuring a plurality of times spectral properties of samples of a healthy biological tissue (individual component analysis). FIG. 3 illustrates a graph of an analysis result (N=3) of the individual component of the spectral property of a mucous membrane of a stomach shown in FIG. 2.

Figure 4:
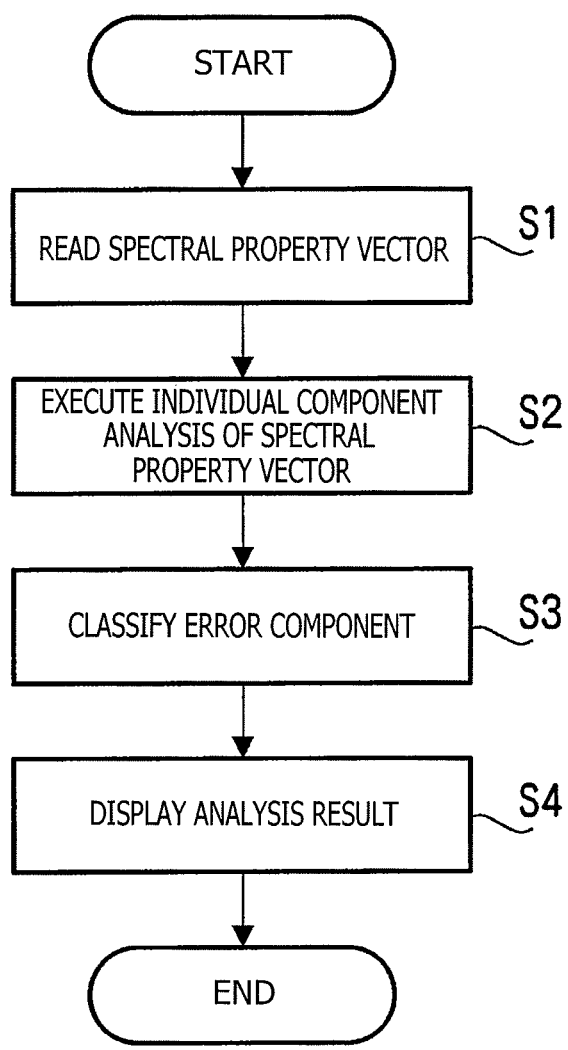
FIG. 4 is a flowchart of an analysis program according to the embodiment.

FIG. 4 is a flowchart illustrating the analysis program according to the embodiment. When the analysis program is executed, step S1 is processed. In step S1, the CPU 311 reads the spectral property vector A measured by the spectrometer 220. The spectral property vector A may be obtained from the spectrometer 220 when the analysis program is executed, or may be obtained by reading the spectral property vector which has been measured in advance by the spectrometer 220 and stored, for example, in the storage 313.

Next, the process proceeds to step S2, in step S2, the CPU 311 executes the multiple linear regression analysis with respect to the spectral property vector of the particular biological tissue, using the individual component vector $\varepsilon_n$ which has been obtained in advance by the individual component analysis, and calculates the coefficient $s_n$ and the error component E. As techniques for the multiple linear regression analysis, known techniques including a conjugate gradient method, a least-square method, a damped least-square method, Newton's method or quasi-Newton method may be used.

Next, the process proceeds to step S3. In step S3, the CPU 311 classifies the obtained error component E. Specifically, the CPU 311 has executed the multiple linear regression analysis with respect to the spectral property vectors of a plurality of biological tissues each of which has been judged to have a particular affected area, and has determined in advance a typical error component $E_d$ in the particular affected area. Then, for the error component E, the CPU 311 determines the coefficient $s_d$ satisfying a following expression 3 using the error component $E_d$.

$$E \approx s_d E_d \quad \text{(Expression 3)}$$

Then, the CPU 311 determines the similarity D between a vector $E_d = [E_{d\lambda 1}, E_{d\lambda 2}, \ldots E_{d\lambda M}]$ and a vector $E/s_d = [E_{\lambda 1}/s_d, E_{\lambda 2}/s_d, \ldots E_{\lambda M}/s_d]$ obtained by dividing the error component vector E by $s_d$, using a following expression (4).

$$D = \sum_{m=1}^{M} w_{\lambda m} \cdot \left( E_{d\lambda m} - \frac{E_{\lambda m}}{s_d} \right)^2 \quad \text{(Expression 4)}$$

The coefficient $w_{\lambda m}$ is a weighing coefficient determined by an empirical rule, and aims at highlighting the similarity between shapes of the vectors E and $E_d$ at a particular frequency.

It can be said that, as the obtained similarity D approaches zero, the possibility that the biological tissue indicated by the error component E has the particular affected area indicated by the error component $E_d$ becomes higher. The analysis program makes a judgment on whether the biological tissue corresponding to the error component E has the particular affected area corresponding to the error component $E_d$, based on a similarity $D_{dk}$ between the error component $E_d$ and a vector $E_{dk}/s_{dk} = [E_{dk\lambda 1}/s_{dk}, E_{dk\lambda 2}/s_{dk}, \ldots E_{dk\lambda M}/s_{dk}]$ (k=1, 2, \ldots, K) which is obtained by dividing an error component $E_{dk}$ of a sample used to obtained the error component $E_d$ by a ratio $S_{dk}$ of $E_{dk}$ with respect to $E_d$. The similarity $D_{dk}$ has been determined in advance based on a following expression (5).

$$E_{dk} \approx s_{dk} E \quad \text{(Expression 5)}$$

$$D_{dk} = \sum_{m=1}^{M} w_{\lambda m} \cdot \left( W_{\lambda m} - \frac{E_{dk\lambda k}}{s_{dk}} \right)^2$$

The analysis program conducts a test regarding whether the set $D_{dk}$ of the similarity determined from the error components $E_{dk}$ of a number of simples includes the similarity D determined from the error component E. For example, the analysis program calculates the possibility that the set $D_{dk}$ includes the similarity D. Alternatively, the analysis program determines the confidence interval of the set Ddk, and makes a judgment on whether the biological tissue corresponding to the error component E includes the particular affected area in accordance with whether the similarity D is included in the determined confidence interval. For example, when the similarity D is included in 99.8% confidence interval, the analysis program determines that there is a possibility that the biological tissue corresponding to the error component E includes the affected area. Furthermore, when the similarity D is included in 66.2% confidence interval and is not included in 99.8% confidence interval, the analysis program judges that re-test is necessary.

Then, the process proceeds to step S4. In step S4, the CPU 311 displays the analysis result data (the possibility that the similarity D is included in the set $D_{dk}$, or the judgment result based on the confidence interval) by the above described test on the analysis result displaying monitor 320 (FIG. 1) as described above. Next, the CPU 311 terminates the analysis program. A doctor who is a user of the auxiliary diagnostic system 1 makes a diagnosis while referring to the analysis result displayed on the analysis result displaying monitor 320.

It should be noted that the electronic endoscope processor 120 according to the embodiment includes a CPU which totally controls the components including the signal processing circuit 121 and the light source unit 122 accommodated in the electronic endoscope processor 120, and an I/O controller which communicates with the I/O controller 312 of the analysis computer 310 while receiving an input from the operation unit 112 of the electronic endoscope 110. The analysis program according to the embodiment is configured to be executed based on the input from the operation unit 112.

What is claimed is:

1. An auxiliary diagnostic apparatus, comprising:
a vector inputter that reads a test vector which is a spectral property vector of a biological tissue targeted for a diagnosis;
a multiple linear regression analyzer that executes a multiple linear regression analysis for the test vector with a plurality of individual component vectors which are spectral property vectors of particular substances, and obtains an error vector which is a vector of a residual error component; and
an indicator calculator that extracts a feature of the error vector, and, from the extracted feature, calculates an indicator indicating an affected area included in the biological tissue targeted for the diagnosis and which type of affected area is included in the biological tissue.

2. The auxiliary diagnostic apparatus according to claim 1, wherein the individual component vectors are calculated by an individual component analysis from spectral property vectors of a plurality of biological tissue samples each of which corresponds to a same portion of the biological tissue targeted for the diagnosis and which does not include an affected area.

3. The auxiliary diagnostic apparatus according to claim 1, wherein the indicator calculator calculates the indicator based on an affected area substance vector obtained by the individual component analysis from affected area sample error vectors which are vectors of residual error components obtained by executing, with the plurality of individual component vectors, the multiple linear regression analysis for spectral property vectors of a plurality of biological tissue samples including particular affected areas.

4. The auxiliary diagnostic apparatus according to claim 3, wherein the indicator calculator operates to:
calculate, by the multiple linear regression analysis, a coefficient $s_d$ satisfying a following expression (a):

$$E \approx s_d E_d \quad (a)$$

where the error vector is defined as $E=[E_{\lambda 1}, E_{\lambda 2}, \ldots E_{\lambda M}]$ and the affected area substance vector is defined as $E_d = [E_{d\lambda 1}, E_{d\lambda 2}, \ldots E_{d\lambda M}]$;
calculate, using a weighing coefficient $w_{\lambda m}$, a similarity D between vectors $E/s_d$ and $E_d$ through a following expression (b):

$$D = \sum_{m=1}^{M} w_{\lambda m} \cdot \left(E_{d\lambda m} - \frac{E_{\lambda m}}{s_d}\right)^2; \quad (b)$$

and
determine the indicator based on the similarity D.

5. The auxiliary diagnostic apparatus according to claim 4, wherein the indicator calculator operates to:
calculate a probability that the similarity D is included in a similarity group $D_{dk}$, by a test based on a coefficient $s_{dk}$, satisfying a following expression (c) and obtained by the multiple linear regression analysis while defining the plurality of affected area sample error vectors as $E_{dk} = [E_{dk\lambda 1}, E_{dk\lambda 2}, \ldots E_{dk\lambda M}]$ (k=1, 2, ..., K), and the similarity group $D_{dk}$ between $E_d$ and respective ones of vectors $E_{dk}/s_{dk}$ obtained by a following expression (d); and
define the probability that the similarity D is included in the similarity group $D_{dk}$ as the indicator, $$E_{dk} \approx s_{dk} E_d \quad (c)$$

$$D_{dk} = \sum_{m=1}^{M} w_{\lambda m} \cdot \left(E_{d\lambda m} - \frac{E_{dk\lambda k}}{s_{dk}}\right)^2. \quad (d)$$

6. An auxiliary diagnostic method, comprising:
reading, using a processor, a test vector which is a spectral property vector of a biological tissue targeted for a diagnosis;
executing, using the processor, a multiple linear regression analysis for the test vector with a plurality of individual component vectors which are spectral property vectors of particular substances, and obtaining an error vector which is a vector of a residual error component;
extracting, using the processor, a feature of the error vector, and, from the extracted feature, calculating an indicator indicating an affected area included in the biological tissue targeted for the diagnosis and which type of affected area is included in the biological tissue.

7. The auxiliary diagnostic method according to claim 6, wherein the individual component vectors are calculated by an individual component analysis from spectral property vectors of a plurality of biological tissue samples each of which corresponds to a same portion of the biological tissue targeted for the diagnosis and which does not include an affected area.

8. The auxiliary diagnostic method according to claim 6, wherein the calculating includes calculating the indicator based on an affected area substance vector obtained by the individual component analysis from affected area sample error vectors which are vectors of residual error components obtained by executing, with the plurality of individual component vectors, the multiple linear regression analysis for spectral property vectors of a plurality of biological tissue samples including particular affected areas.

9. The auxiliary diagnostic method according to claim 8, wherein, the calculating includes,
calculating, by the multiple linear regression analysis, a coefficient $s_d$ satisfying a following expression (a):

$$E \approx s_d E_d$$

where the error vector is defined as $E=[E_{\lambda 1}, E_{\lambda 2}, \ldots E_{\lambda M}]$ and the affected area substance vector is defined as $Ed=[E_{d\lambda 1}, E_{d\lambda 2}, \ldots E_{d\lambda M}]$;

calculating, using a weighing coefficient $w_{\lambda m}$, a similarity D between vectors $E/s_d$ and $E_d$ through a following expression (b):

$$D = \sum_{m=1}^{M} w_{\lambda m} \cdot \left(E_{d\lambda m} - \frac{E_{\lambda m}}{s_d}\right)^2; \tag{b}$$

and determining the indicator based on the similarity D.

10. The auxiliary diagnostic method according to claim 9, wherein, the calculating includes, calculating a probability that the similarity D is included in a similarity group $D_{dk}$, by a test based on a coefficient $s_{dk}$, satisfying a following expression (c) and obtained by the multiple linear regression analysis while defining the plurality of affected area sample error vectors as $E_{dk}=[E_{dk\lambda 1}, E_{dk\lambda 2}, \ldots E_{dk\lambda M}]$ (k=1, 2, ..., K), and the similarity group $D_{dk}$ between $E_d$ and respective ones of vectors $E_{dk}/s_{dk}$ obtained by a following expression (d); and defining the probability that the similarity D is included in the similarity group $D_{dk}$ as the indicator, $$E_{dk} \approx s_{dk} E_d \tag{c}$$

$$D_{dk} = \sum_{m=1}^{M} w_{\lambda m} \cdot \left(E_{d\lambda m} - \frac{E_{dk\lambda k}}{s_{dk}}\right)^2. \tag{d}$$

* * * * *